United States Patent [19]

Enscore et al.

[11] Patent Number: 4,938,759
[45] Date of Patent: Jul. 3, 1990

[54] TRANSDERMAL DELIVERY DEVICE HAVING A RATE CONTROLLING ADHESIVE

[75] Inventors: David J. Enscore, Sunnyvale; Eun S. Lee, Redwood City; Su I. Yum, Los Altos, all of Calif.

[73] Assignee: Alza Corporation, Palo Alto, Calif.

[21] Appl. No.: 903,002

[22] Filed: Sep. 2, 1986

[51] Int. Cl.$^5$ ............................................. A61K 9/00
[52] U.S. Cl. .................................. 604/896.1; 424/449
[58] Field of Search ................ 604/896, 897, 303–309, 604/890, 443, 447–449; 128/82, 155–156; D24/34, 49; 424/427, 429, 443, 447, 448, 449

[56] References Cited

U.S. PATENT DOCUMENTS

| | | | |
|---|---|---|---|
| 3,699,963 | 10/1972 | Zaffaroni | 604/304 |
| 3,742,951 | 7/1973 | Zaffaroni | 604/304 |
| 3,797,494 | 3/1974 | Zaffaroni | 604/897 |
| 3,926,188 | 12/1975 | Baker et al. | 604/294 |
| 3,964,482 | 6/1976 | Gerstel et al. | 604/896 |
| 4,031,894 | 6/1977 | Urquhart et al. | 604/897 |
| 4,060,084 | 11/1977 | Chandrasekaran et al. | 128/260 |
| 4,144,317 | 3/1979 | Higuchi et al. | 424/449 |
| 4,286,592 | 9/1981 | Chandrasekaran | 128/156 |
| 4,314,557 | 2/1982 | Chabdrasekaran | 128/260 |
| 4,605,548 | 8/1986 | Ushiyama et al. | 424/449 |
| 4,615,699 | 9/1986 | Gale et al. | 424/449 |
| 4,627,852 | 12/1986 | von Bittera et al. | 604/304 |
| 4,752,478 | 6/1988 | Bondi et al. | 424/449 |

FOREIGN PATENT DOCUMENTS

| | | |
|---|---|---|
| 0033615 | 8/1981 | European Pat. Off. . |
| 0186071 | 2/1986 | European Pat. Off. . |
| 2093694 | 9/1982 | United Kingdom . |

OTHER PUBLICATIONS

Journal of Macromolecular Science Review of Macromolecular Chemistry and Physics C23(1), pp. 61, 62, 85, 86 (1983).

Primary Examiner—C. Fred Rosenbaum
Assistant Examiner—Sharon Rose
Attorney, Agent, or Firm—Steven F. Stone; Edward L. Mandell; Paul L. Sabatine

[57] ABSTRACT

A transdermal delivery device having a release-rate controlling-adhesive is disclosed having improved delivery characteristics. The device employs a polyisobutylene/mineral oil adhesive formulation and an ethylene/vinyl acetate (EVA) drug reservoir formulation. The device is useful in delivering a wide variety of transdermally administrable drugs, particularly those which are moderately soluble in mineral oil. Preferred embodiments deliver timolol base and atropine base from an EVA (40% VA) reservoir formulation.

34 Claims, 3 Drawing Sheets

RELEASE RATE DATA FROM EXAMPLE 1
(EVA 40 RESERVOIR PIB/MO ADHESIVE)

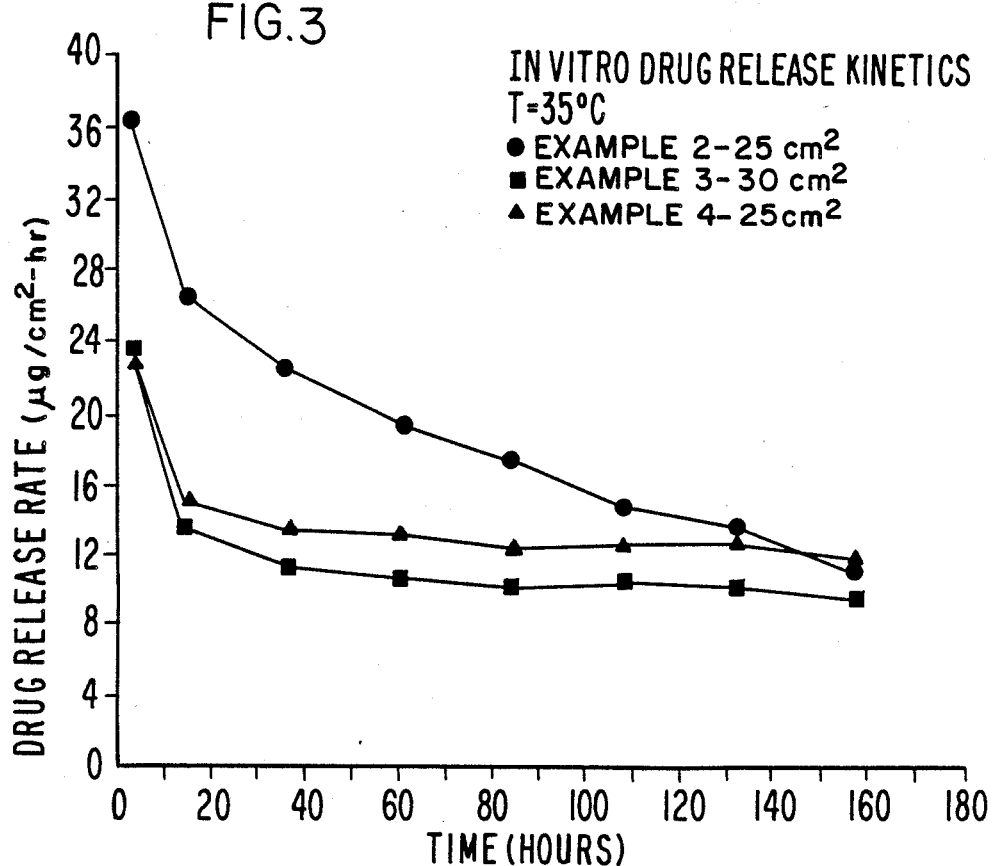
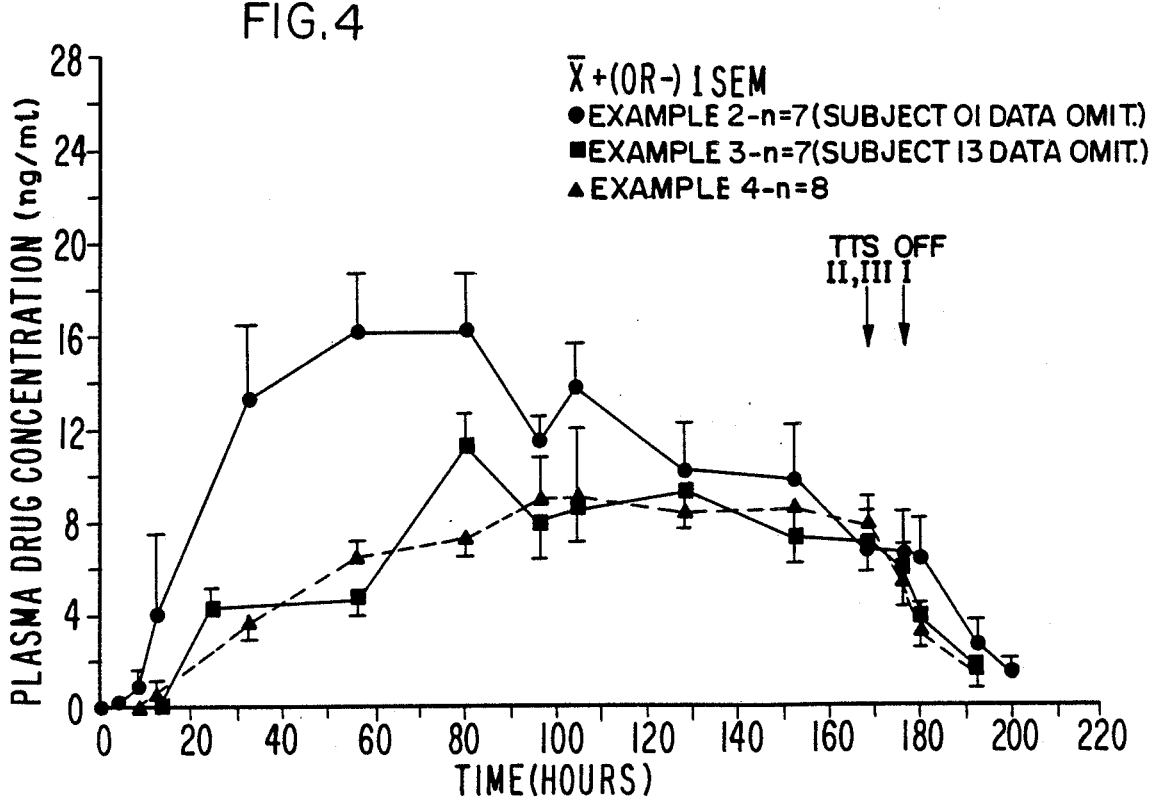

THEORETICAL COMPARISON TRP-18 SYSTEMS WITH DIFFERENT DRUG RESERVOIRS (32°C)

TRANSDERMAL DELIVERY DEVICE HAVING A RATE CONTROLLING ADHESIVE

FIELD OF THE INVENTION

This invention relates to medical devices to be applied to the skin to administer biologically active agents at substantially constant rates using release-rate controlling adhesives.

BACKGROUND OF THE INVENTION

Various types of bandages for delivering biologically active agents (hereafter referred to generally as "drugs") to the skin at substantially constant rates are known to the art and have been proposed to deliver a wide variety of drugs. As used herein the term "drug" is intended to have its broadest interpretation as any biologically active substance which is administered to a subject to produce a usually beneficial biological effect. U.S. Pat. No. 3,598,122 (which is hereby incorporated by reference) for example, describes a multi-layered bandage comprising a backing layer, a drug reservoir layer, a release-rate controlling membrane and a contact adhesive layer which maintains the bandages in drug delivering contact with the skin. The release-rate controlling element is disposed between the drug and the contact adhesive layer and constitutes a separate element of the device.

U.S. Pat. No. 4,286,592 (which is hereby incorporated by reference) constitutes a significant improvement in this technology by combining into one structural element of the device the function of both the contact adhesive and the rate-controlling membrane. According to this patent, in order to permit the contact adhesive layer to function as both a contact adhesive and a rate-controlling element, a relationship between the diffusion coefficients and solubilities of the drug in the adhesive and the drug reservoir and the thickness of the adhesive must exist. This relationship is defined as follows and which, for convenience will be referred to hereafter as the "Rate Controlling Adhesive Relationship."

(i) the concentration of the drug in the contact adhesive lamina, $C_{CA}$(mg/cm$^3$), is not greater than the solubility of the drug in the contact adhesive composition, $C_{SCA}$, and (ii) the ratio $$\frac{D_{CA} C_{SCA}}{l_{CA} \cdot \left( \frac{D_{DR} C_{DR} C_{SDR}}{t} \right)^{\frac{1}{2}}}$$

is in the range of about 0.01 to about 0.7 over a substantial portion of the adminsitration period and wherein:

$D_{CA}$ is the diffusion coefficient of the drug in the contact adhesive composition in cm$^2$/hr, $l_{CA}$ is the thickness of the contact adhesive lamina in cm, $D_{DR}$ is the diffusion coefficient of the drug in the carrier in cm$^2$/hr, $C_{DR}$ is the concentration of drug in the drug reservior in mg/cm$^3$ $C_{SDR}$ is the solubility of the drug in the carrier in mg/cm$^3$, and t, is any time during said administration period in hours, and the term "substantial" as applied to said time period means at least 50%. When the conditions set forth in the Rate-Controlling Relationship are met, the flux of drug from the drug reservoir layer, in the absence of the adhesive layer, will be about 100 times greater than the flux of drug through the adhesive layer when the value of the Relationship is 0.01. When the value of the Relationship is increased to 0.7 the flux of drug from the reservoir layer will have been reduced to a level equal to the flux of drug through the adhesive. This provides a simple laboratory test to determine whether or not the relationship is met without requiring the determination of the values for the individual parameters of the relationship. The in vitro flux of drug can be measured for samples of the reservoir and adhesive compositions and as long as the reservoir flux is from 1 to about 100 times the adhesive flux the relationship will be satisfied.

Of the embodiments disclosed in this patent, the embodiment of Example 1 utilizes similar polyisobutylene/mineral oil (PIB/MO) compositions for both the drug reservoir and adhesive layers. The embodiment of Example 2 utilizes dissimilar materials, silicone oil and an ethylene vinylacetate (EVA) copolymer (9% VA) as the reservoir and adhesive, respectively. The embodiment of Example 1, possesses better characteristics in terms of structural integrity and adhesive properties but, as disclosed in the patent, the diffusion coefficient and solubility of the agent through the drug reservoir and the adhesive layers of Example 1 are substantially the same. The release characteristics of the device of Example I could be improved if the matrix or carrier composition of the drug reservoir possessed a substantially higher permeability than the contact adhesive composition, as in Example 2, but by so doing some compromises in structural integrity and adhesive properties are made.

One of the desirable characteristics of PIB/MO adhesives (as used herein, "mineral oil" includes both natural and synthetic mineral oils), is their high permeability to many drugs. For this reason, prior to our invention, we were unaware of any transdermal delivery device which conformed to the Rate Controlling Adhesive Relationship which utilized a drug reservoir matrix composition other than a PIB/MO composition in combination with a PIB/MO adhesive. According to our invention we have provided a combination of dissimilar reservoir and adhesive compositions which enable the devices of our invention to use a PIB/MO adhesive and also posses improved the long-term release characteristics.

It is accordingly an object of this invention to provide improved transdermal delivery devices employing release-rate controlling adhesives.

It is another object of this invention to provide a combination of a drug reservoir matrix material with a PIB/MO adhesive material which permit a drug delivery device to conform to the Rate Controlling Adhesive Relationship.

It is another object of this invention to provide a transdermal delivery device for administering timolol.

It is another object of this invention to provide a transdermal delivery device for administering atropine.

These and other objects of the invention will be readily apparent from the following description with reference to the accompanying drawings wherein:

DESCRIPTION OF THE DRAWINGS

FIG. 3 contain plots of in vitro delivery characteristics of embodiments of this invention;

FIG. 4 contains plots of in vivo plasma levels obtained from embodiments of this invention.

DESCRIPTION OF THE INVENTION

Figure 1:
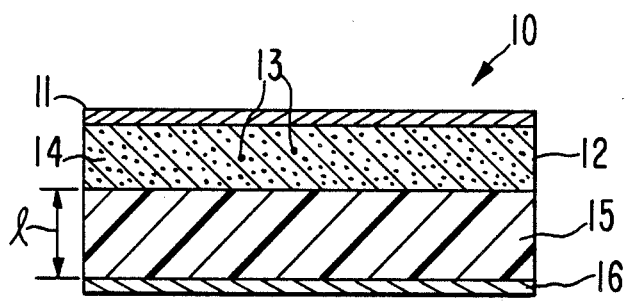
FIG. 1 is a cross sectional view through an embodiment of this invention.

FIG. 1 illustrates the basic structure of the device of this invention, generally designated as bandage 10 before it is applied to the skin. The components of the device are, from the top, an impermeable backing layer 11, a drug reservoir layer 12 comprising the biologically active agent to be delivered dispersed in a carrier 14 (which reservoir layer may also contain permeation enhancers, thickeners, stabilizing agents and other additives as known to the art), a contact adhesive layer 15, and an impermeable strippable coating or release liner 16. Layer 16 is removed to expose layer 15 before the bandage 10 is applied to the skin. Depending on the particular drug and other components of the device, it may, in some cases, be desirable to enclose the sides of bandage 10 with an impermeable coating or otherwise seal the sides to prevent one or more of the components from evaporating, bleeding, exuding, leaking or otherwise exiting from the exposed side surfaces. Backing layer 11 prevents the drug from being released from the top surface of reservoir 12 and it also serves as a protective layer coating for the device when it is in place on the skin or mucosa. As such it must be impermeable both to water and to the materials contained in the drug reservoir and suitable materials for making such backing members are known to the prior art, see for instance, U.S. Pat. No. 3,598,122, Column 5, lines 56-71. Drug reservoir 12 is composed of a mixture of the carrier and drug and in most instances the drug will initially be present in excess of its solubility in the carrier material. In such a case the drug would initially be present in the reservoir in both dissolved and undissolved form, excess undissolved drug constituting drug depots for maintaining the reservoir at unit activity throughout its intended dispensing life. The amount of the excess drug therefor determines the overall useful life of the device and drug may be present in amounts up to that at which the carrier ceases to be the continuous phase through which the drug is dispersed. The maximum drug content normally achievable is in the range of 35 to 50% by volume in the reservoir. In the adhesive layer, however, the drug is not at a concentration above saturation during steady-state operation.

As disclosed in U.S. Pat. No. 4,286,592, in order to permit the contact adhesive layer 15 to function as both a contact adhesive and a rate controlling element, the drug resevoir and adhesive layers should conform to the Rate Controlling Adhesive Relationship.

According to our invention we utilize a PIB/MO contact adhesive preferably comprising a blend of low molecular weight (LMW) PIB (35,000 to 50,000 viscosity average molecular weight) and high molecular weight (HMW) PIB (1,000,000 to 1,500,000 viscosity average molecular weight) and a natural or synthetic mineral oil having a viscosity of 10 to 100 cp at 25° C. Preferred mixtures comprise 35 to 65% MO, 10 to 40% LMW PIB and 10 to 40% HMW PIB. These compositions are known to the art to be excellent adhesives for transdermal delivery devices such as shown in U.S. Pat. No. 4,286,597 noted above and in Pat. No. 4,262,003, for example, and which is incorporated herein by reference.

According to our invention, the carrier for the drug reservoir comprises an EVA copolymer having a vinyl acetate content of about 25% to about 60% by weight., the preferred range being from being 28% to 40%. Such polymers are known art and include those disclosed in U.S. Pat. No. 4,144,317 which is incorporated herein by reference.

The combination of drug reservoir and contact adhesive compositions of our invention can be used to deliver numerous transdermally administrable drugs. To obtain maximum benefit from this invention the drug should have a permeability through the EVA reservoir which is higher than its diffusion coefficient through the PIB/MO adhesive. Particularly suitable are drugs having melting points of 50° C. or higher, which are moderately soluble in mineral oil (i.e. solubility in the range of 10 mcg/cm$^3$-5 mg/cm$^3$), and include timolol, fentanyl, atropine, clonidine, propranolol, isosorbide dinitrate, scopolamine, estradiol, phenylpropanolamine, ouabain, salbutamol, quanabenz labetolol, haloperidol, bromocryptine, ephedrine, chlorpheniramine and metrifonate, for example.

Having thus generally described our invention, the following specific examples are provided.

EXAMPLE 1

The transdermal administration of timolol has been described as safe and effective by P. H. Vlasses et al, "Initial Evaluation of Transdermal Timolol: Serum Concentration and B-Blockade," *Journal of Cardiovascular Pharmacology*, 7:245-250 (1985).

Transdermal timolol delivery devices according to this invention were fabricated by solvent casting the adhesive composition from methylene chloride and extruding the drug reservoir composition described in Table I (Example 1) onto the release liner and the impermeable backing respectively and laminating the two elements so formed together.

TABLE 1

|  |  | EXAMPLE 1 | CONTROL |
|---|---|---|---|
|  |  | (% by weight) | |
| I. Stripable Release Liner | Siliconized Polyester | | |
| II. Contact Adhesive | LMW PIB | 25.5 (21) | 21 |
| 1.7 mil | HMW PIB | 38.3 (32) | 32 |
| (2.0 mil) | Mineral Oil (Polybutene L-100 460 MW) | 36.2 (47) | 47 |
| III. Drug Reservoir (@5.0 mil) | EVA 40% VA | 46.9 (52) | |
|  | Mineral Oil (Polybutene L-100) | 20.1 (11.4) | |
|  | TiO$_2$ | 3.0 (3.3) | |
|  | Timolol base | 30.0 (33.4) | 30.0 |
|  | LMW PIB | | 22.2 |
|  | HMW PIB | | 14.8 |
|  | Mineral Oil | | 33.0 |

TABLE 1-continued

|  |  | EXAMPLE 1 CONTROL (% by weight) |
|---|---|---|
| IV. Impermeable Backing | (Polybutene L-100) Flesh Colored Medpar Aluminized Polyester |  |

(The oil migrates from the drug reservoir to the contact adhesive during storage to reach the approximate equilibrium concentrations and adhesive thicknesses shown in parentheses.)

Figure 2:
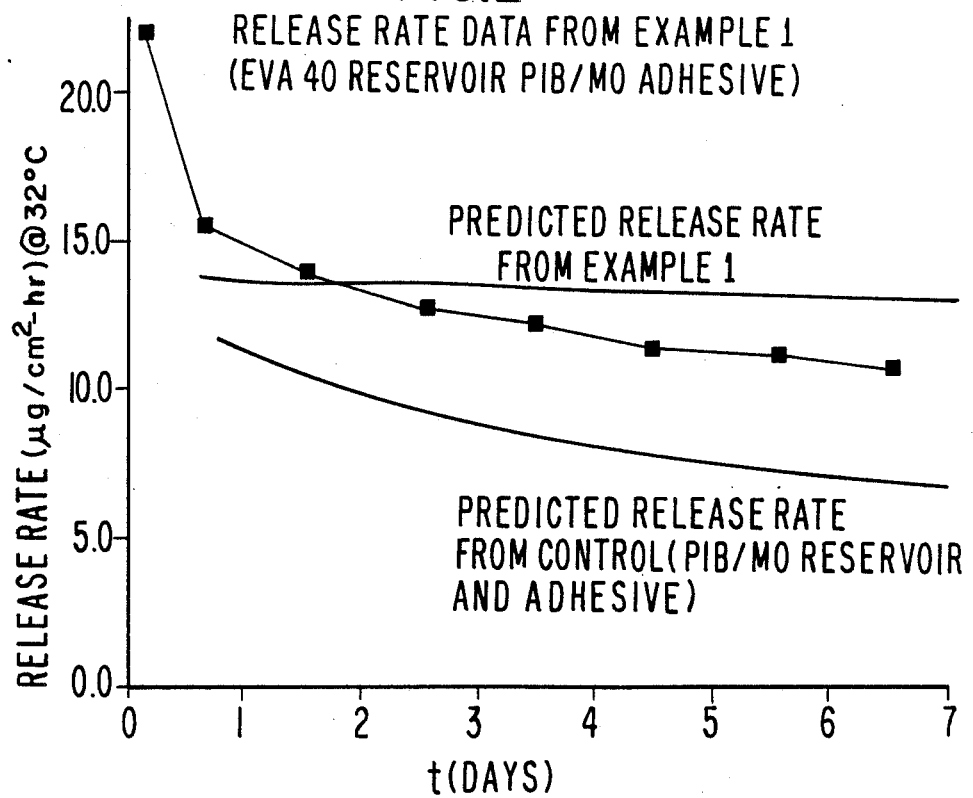
FIG. 2 is a plot comparing theoretical and actual in vitro release rates versus time of a timolol delivery device according to this invention with the theoretical in vitro release rate of a timolol delivery device having a PIB/MO reservoir and adhesive.

The diffusion coefficients at 32° C. of timolol through EVA 40 and the adhesive were about $6.4 \times 10^{-6} cm^2/hr$ and $1.4 \times 10^{-5} cm^2/hr$, respectively. The solubility at 32° C. of timolol in EVA 40 and the PIB/MO adhesives were about 108 mg/cm$^3$ and 11 mg/cm$^3$ respectively. The theoretical and actual in vitro release rates at 32° C. directly into an infinite sink from the device of Example I compared to a the theoretical release rate of a device using the control PIB/MO compositions for both the drug reservoir and adhesive are shown in FIG. 2.

EXAMPLES 2, 3 AND 4

Embodiments of timolol delivery devices were fabricated by solvent casting from methylene chloride and extruding in the manner described in Example 1 from the compositions shown in Table 2:

TABLE 2

|  | EXAMPLE 2 (% by wt) | EXAMPLE 3 (% by wt) | EXAMPLE 4 (% by wt) |
|---|---|---|---|
| DRUG RESERVOIR |  |  |  |
| Thickness as cast | 5.1 mils | 5.5 mils | 5.5 mils |
| EVA 40 | 46.9% | 49.0% | 49.0% |
| Polybutene (L-100) | 20.1% | 13.0% | 13.0% |
| Timolol Base | 30.0% | 35.0% | 35.0% |
| TiO$_2$ | 3.0% | 3.0% | 3.0% |
| ADHESIVE |  |  |  |
| Thickness as Cast | 1.7 mil |  |  |
| Polybutene (L-100) | 36.1% | 41.0% | 42.5%* |
| LMW PIB | 38.3% | 35.4% | 34.5% |
| HMW PIB | 25.6% | 23.6 | 23.0% |
| (Equilibrium thickness) | (2.0 mils) | (30 mils) | (2.0 mils) |
| Size | 25 cm$^2$ | 30 cm$^2$ | 25 cm$^2$ |

The in vitro release rates of such devices into an infinite sink at 35° C. is shown in FIG. 3. The devices were applied to human volunteers and maintained in place for 1 week. Blood samples were taken periodically and assayed for timolol content. The results are shown in FIG. 4.

The timol levels obtained from the studies on Example 2 were adequate to produce reduction in exercize heart rate in the range of about 15-26% from hour 20 to hour 168.

EXAMPLE 4

Figure 5:
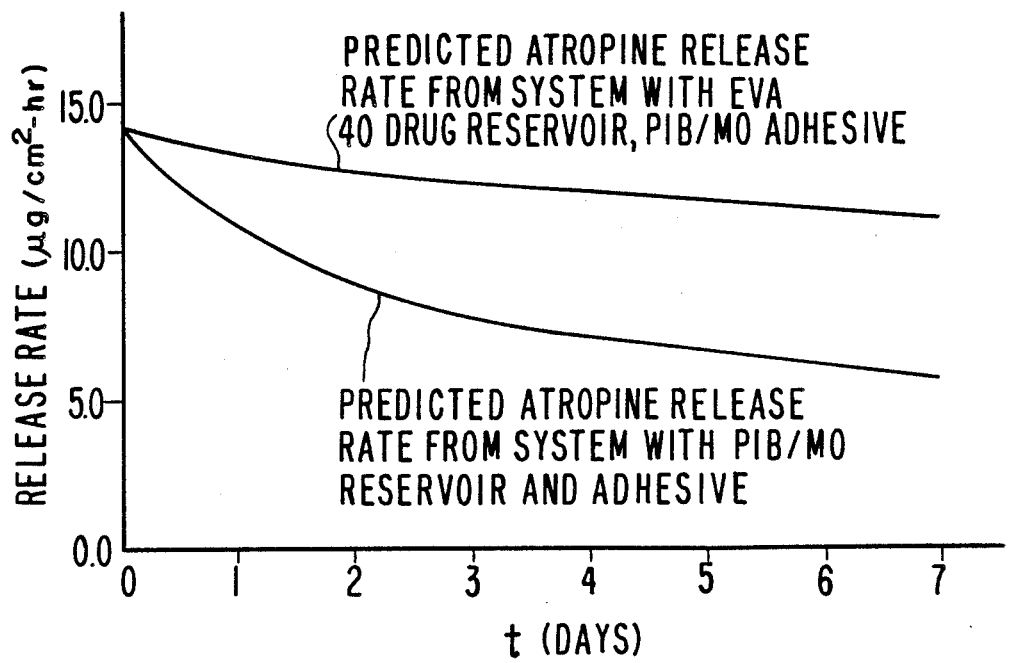
FIG. 5 is a plot comparing theoretical in vitro release rates versus time of an atropine delivery device according to this invention with an atropine delivery device have a PIB/MO reservoir and adhesive.

The theoretical in vitro release rates into an infinite sink from atropine delivery devices having the formulations of Table 3 are compared in FIG. 5.

TABLE 3

|  |  | EXAMPLE 5 (% by weight) | CONTROL |
|---|---|---|---|
| I. Stripable Release Liner | Siliconized Polyester |  |  |
| II. Adhesive 2.0 mil | HMW PIB | 20.3 | 20.3 |
|  | LMW PIB | 25.5 | 25.5 |
|  | Light Mineral Oil Pehreco DRAKEOLS ® | 40.8 | 40.8 |
|  | Fumed Silica | 3.5 | 3.5 |
|  | Atropine base | 9.9 | 9.9 |
| III. Drug Reservoir 2.5 mil | EVA 40% VA | 64.2 |  |
|  | Mineral Oil | 15.8 |  |
|  | Atropine base | 20.0 | 20.0 |
|  | HMW PIB |  | 18.2 |
|  | LMW PIB |  | 22.6 |
|  | Light Mineral Oil |  | 36.2 |
|  | Fumed Silica |  | 3.0 |
| IV. Impermeable Backing | Flesh Colored Medpar Aluminized Polyester |  |  |

The permeabilities of atropine base in EVA 40 and the PIB/MO composition at 32° C. are estimated at $1.3 \times 10^{-1}$ mcg/cm/hr and $5.4 \times 10^{-2}$ mcg/cm/hr, respectively. The permeability of atropine base in the EVA 40-mineral oil reservoir composition at 32° C. is estimated at $3.0 \times 10^{-1}$ mcg/cm/hr. Atropine is included in the adhesive to decrease the lag time for onset of therapeutic blood levels.

Having thus generally described our invention and provided specific examples thereof, it will be apparent that changes and modifications can be made by workers skilled in the art without departing from the scope of our invention which is limited only by the following claims,

We claim:

1. A medical device for the transdermal administration of a drug said device conforming to the Rate Controlling Adhesive Relationship and comprising:
   (a) a drug reservoir comprising a drug dispersed with an ethylene/vinyl acetate copolymer having a vinyl acetate content in the range of about 15-60% by weight; and
   (b) a PIB/MO adhesive for maintaining said reservoir in drug transferring relationship to the skin, said adhesive being bonded to said drug reservoir and being disposed in the path of diffusional flow of drug from said reservoir to the skin such that substantially all drug must pass through the adhesive by diffusion from the reservoir to the skin.

2. The device of claim 1 wherein said vinyl acetate content is in the range of about 28-40% by weight.

3. The device of claim 1 wherein said drug is initially present in said reservoir at a concentration above saturation.

4. The device of claim 1 wherein said drug is moderately soluble in mineral oil and has a melting point above about 50° C.

5. The device of claim 4 wherein said drug is selected from the group consisting of timolol, fentanyl, atropine, clonidine, propranolol, isosorbide dinitrate, scopolamine, estradiol, phenylpropanolamine, ouabain, salbutamol, quanabenz, labetolol, haloperidol, bromocryptine, ephedrine, chlorpheniramine and metrifonate.

6. The device of claim 1 wherein the concentration of said drug in the reservoir is sufficient to maintain the activity of the drug in said carrier at unit activity for a time period in the range of from 24 hours to 7 days.

7. The device of claim 1 wherein said drug is the base form of timolol.

8. The device of claim 7 wherein said ethylene vinyl acetate copolymer has a viny acetate content in the range of about 28-40%.

9. The device of claim 8 wherein said vinyl acetate content is about 40%.

10. The device of claim 1 wherein said drug is the base form of atropine.

11. The device of claim 10 wherein said ethylene/vinyl acetate copolymer has a vinyl acetate content in the range of about 28-40%.

12. The device of claim 11 wherein said vinyl acetate content is about 40%.

13. The device of claim 4 wherein said ethylene/vinyl acetate copolymer has a vinyl acetate content in the range of about 28-40%.

14. The device of claim 13 wherein said vinyl acetate content is about 40%.

15. The device of claim 5 wherein said ethylene/vinyl acetate copolymer has a vinyl acetate content of about 28-40%.

16. The device of claim 15 wherein said vinyl acetate content is about 40%.

17. A medical device for the transdermal delivery of a drug moderately soluble in mineral oil and having a melting point above about 50° C. comprising a laminate of:
(a) an impermeable backing;
(b) a drug reservoir lamina comprising said drug dispersed within an ethylene/vinyl acetate polymer at a concentration above the saturation concentration of said drug in said polymer, said polymer having a vinyl acetate content in the range of about 15-60%; and
(c) a release-rate controlling adhesive lamina comprising a MO/PIB adhesive.

18. The device of claim 17 wherein said drug is contained in said reservoir at a concentration sufficient to maintain the activity of said drug in said polymer at an activity of one for a period of time in the range of 24 hours to 7 days.

19. The device of claim 17 wherein said vinyl acetate content is in the range of from about 28-40%.

20. The device of claim 17 wherein said vinyl acetate content is about 40%.

21. The device of claim 20 wherein said drug is contained in said reservoir at a concentration sufficient to maintain the activity of said drug in said polymer at an activity of one for a period of time in the range of 24 hours to 7 days.

22. The device of claim 17 further comprising a release-liner lamina forming the surface of the device opposite said impermeable backing.

23. A medical device for the transdermal delivery of timolol comprising a laminate of:
(a) an impermeable backing;
(b) a timolol reservoir lamina comprising timolol base dispersed within an ethylene/vinyl acetate polymer at a concentration above the saturation concentration of said timolol base in said polymer, said polymer having a vinyl acetate content in the range of about 15-60%; and
(c) a release-rate controlling adhesive lamina comprising a MO/PIB adhesive.

24. The device of claim 23 wherein said drug is contained in said reservoir at a concentration sufficient to maintain the activity of said drug in said polymer at an activity of one for a period of time in the range of 24 hours to 7 days.

25. The device of claim 23 wherein said vinyl acetate content is in the range of from about 28-40%.

26. The device of claim 23 wherein said vinyl acetate content is about 40%.

27. The device of claim 26 wherein said drug is contained in said reservoir at a concentration sufficient to maintain the activity of said drug in said polymer at an activity of one for a period of time in the range of 24 hours to 7 days.

28. The device of claim 23 further comprising a release-liner lamina forming the surface of the device opposite said impermeable backing.

29. A medical device for the transdermal delivery of atropine comprising a laminate of:
(a) an impermeable backing;
(b) a atropine reservoir lamina comprising atropine base dispersed within an ethylene/vinyl acetate polymer at a concentration above the saturation concentration of said atropine base in said polymer, said polymer having a vinyl acetate content in the range of about 15-60%; and
(c) a release-rate controlling adhesive lamina comprising a MO/PIB adhesive.

30. The device of claim 29 wherein said drug is contained in said reservoir at a concentration sufficient to maintain the activity of said drug in said polymer at an activity of one for a period of time in the range of 24 hours to 7 days.

31. The device of claim 29 wherein said vinyl acetate content is in the range of from about 28-40%.

32. The device of claim 29 wherein said vinyl acetate content is about 40%.

33. The device of claim 32 wherein said drug is contained in said reservoir at a concentration sufficient to maintain the activity of said drug in said polymer at an activity of one for a period of time in the range of 24 hours to 7 days.

34. The device of claim 29 further comprising a release-liner lamina forming the surface of the device opposite said impermeable backing.

* * * * *